Figure 1:
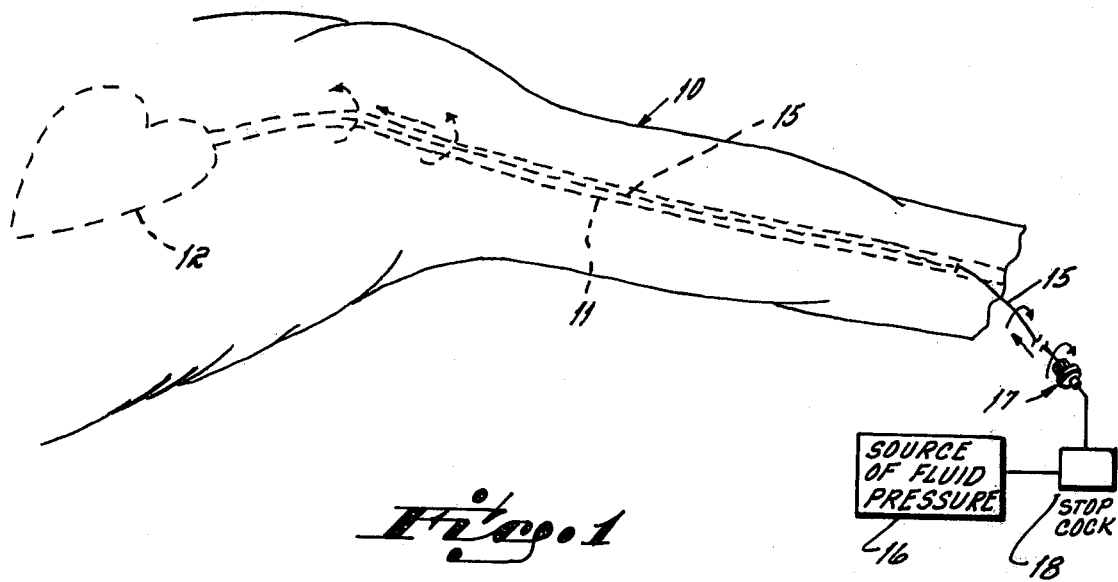

United States Patent [19]

Waldbillig

[11] 4,254,773
[45] Mar. 10, 1981

[54] SWIVEL COUPLING FOR A CATHETERIZATION SYSTEM

[75] Inventor: Charles C. Waldbillig, Upper Arlington, Ohio

[73] Assignee: Medex Inc., Hilliard, Ohio

[21] Appl. No.: 963,184

[22] Filed: Nov. 24, 1978

[51] Int. Cl.³ ............................................. A61M 25/00
[52] U.S. Cl. ................................. 128/348; 128/247; 128/DIG. 9; 285/281
[58] Field of Search ........................ 128/348–351, 128/DIG. 9, 214 R, 247; 285/278, 280, 281, DIG. 22

[56] References Cited

U.S. PATENT DOCUMENTS

| | | | |
|---|---|---|---|
| 2,542,701 | 2/1951 | Press | 285/281 X |
| 2,560,263 | 7/1951 | Wiegand et al. | 285/281 X |
| 2,570,406 | 10/1951 | Troskin et al. | 285/281 X |
| 2,893,395 | 7/1959 | Buck | 128/349 R |
| 2,963,304 | 12/1960 | Comlossy et al. | 285/281 X |
| 3,503,385 | 3/1970 | Stevens | 128/DIG. 9 |
| 3,785,683 | 1/1974 | Adehed | 128/214 R X |
| 3,799,589 | 3/1974 | Boelkins | 285/281 |
| 3,957,293 | 5/1976 | Rodgers | 285/174 |
| 4,152,017 | 5/1979 | Abramson | 285/280 X |

Primary Examiner—Dalton L. Truluck
Attorney, Agent, or Firm—Wood, Herron & Evans

[57] ABSTRACT

A two-piece swivel coupling for a catheter system having Luer connections on either end of the coupling. One piece has a recess which receives an O-ring and the other piece has a spigot which projects through the O-ring into a recess. The O-ring provides radial, fluid-tight interference between the spigot and the recess. Means are provided for preventing the pieces from axially compressing the O-ring so that one piece is freely rotatable with respect to the other as the catheter is inserted in a blood vessel through a tortuous path into a patient's heart.

8 Claims, 2 Drawing Figures

U.S. Patent

Mar. 10, 1981

4,254,773

SWIVEL COUPLING FOR A CATHETERIZATION SYSTEM

This invention relates to a swivel coupling and particularly to a coupling for a catheter system.

BACKGROUND OF THE INVENTION

In a radiological catheterization system procedure, a catheter is inserted into the heart of a patient and a dye is passed into the heart from a fluid pressure source. To get the catheter into the heart, it is inserted in a blood vessel in the patient's arm and is forced through the blood vessel into the heart. The path to the heart is not direct and the catheter must be rotated in order to find its way through the tortuous path. There is a need to connect the catheter to the source of fluid and thereafter thread the catheter into the heart without disconnecting the catheter, for the disconnecting of the catheter might expose the otherwise antiseptic catheter to bacteria during the insertion process.

To accommodate this need for rotating the catheter while maintaining the connection to the source of fluid, swivel couplings or rotators have been provided. One such coupling is made up of metal parts. Following the catheter procedure, the metal coupling must be disassembled, the parts cleaned, lubricated and reassembled.

Another available rotator is made of plastic and is disposable, but is is a three-piece construction and is expensive.

BRIEF DESCRIPTION OF THE INVENTION

The objective of the present invention has been to provide an inexpensive swivel coupling adapted for use in a catheter procedure, the coupling being freely rotatable while at the same time providing fluid-tight integrity, that is, being capable of withstanding fluid under pressure in excess of 700 psi without leakage.

The objective of the invention is achieved by providing two polycarbonate plastic pieces (Lexan) which are sealed by an O-ring. One plastic piece has a recess adapted to receive the O-ring with an interference fit between the outside diameter (O.D.) of the O-ring and the recess wall. The other plastic piece has a spigot which is inserted through the O-ring into the recess. The O-ring has an interference fit with the spigot thus forming a fluid-tight seal between the spigot and the recess.

The two pieces are provided with abutting surfaces which limit axial movement toward each other and thereby preclude any compression in an axial direction of the O-ring under no pressure conditions. The elimination of any axial compression of the O-ring permits the two elements to rotate freely with respect to each other while the radial interference of the O-ring with respect to the recess and the spigot provides the fluid-tight seal.

When fluid under pressure contacts the O-ring, it tends to compress the O-ring in the axial direction, thereby tending to increase its O.D. and decrease its inside diameter (I.D.) thereby making the seal tighter as the pressure increases. The swivel coupling has been tested to 700 psi and it is expected that it will provide a fluid-tight seal at 1200 psi of pressure.

A second recess is provided adjacent the recess which receives the O-ring. The spigot projects beyond the O-ring recess into the second recess thereby minimizing the possibility of the cocking of one piece with respect to the other, thereby increasing the security of assembly of the two plastic pieces.

One piece is provided with a collar and a radially inwardly-directed lip. The other piece has a flange which is insertable past the lip into the collar to snap two pieces together. The flange is tapered so as to facilitate the assembly. The flange and collar connection, coupled with the spigot and recess fit, provides a somewhat loose fit which admits of the free rotation of one piece with respect to the other but which, nevertheless, prevents the pieces from cocking or coming apart during the manipulation of the rotator in the catheterization procedure.

Figure 2:
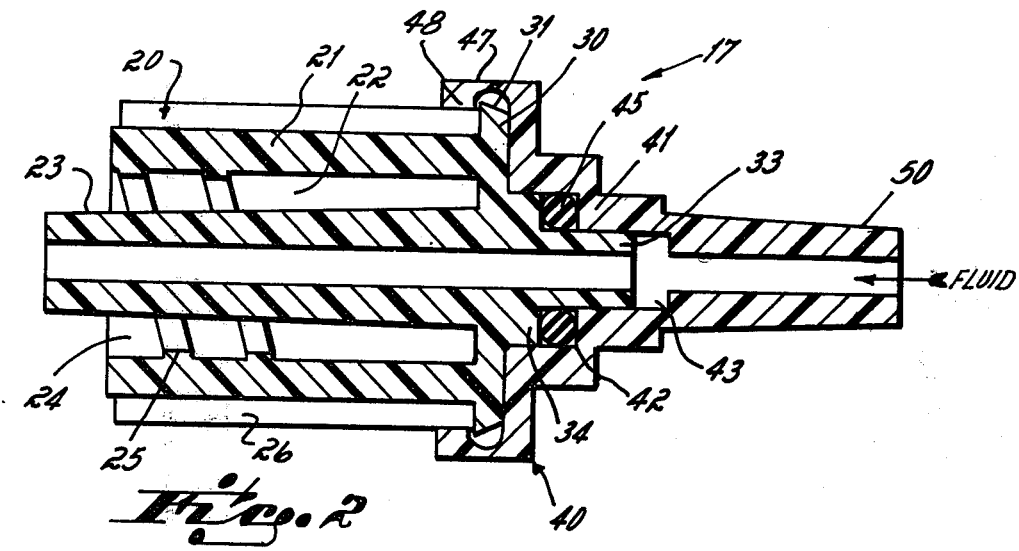

The several features of the invention will become more readily apparent from the following detailed description taken in conjunction with the accompanying drawings in which:

FIG. 1 is a diagrammatic view of the catheterization system for use with a patient; and FIG. 2 is a cross-sectional view of the swivel coupling.

Referring to FIG. 1, there is a diagrammatic illustration of a patient having an arm 10, a blood vessel 11 (artery) in the arm extending to the patient's heart 12. An elongated catheter 15 is shown in the process of being passed through the blood vessel into the heart. The catheter 15 is connected to a source of fluid pressure 16 by way of a swivel coupling 17 and a stopcock system 18 to control the fluids to the heart.

In the operation of the invention, the system is connected as shown and fluid is passed through the system to clear air from the system. The fluid is shut off by means of the stopcock system 18 and the catheter is inserted into the blood vessel. As the catheter is thrust toward the heart, it is rotated in order to help the catheter seek its way along the tortuous path through the blood vessel into the heart by rotating it. The rotation of the catheter is accomplished by rotating one piece of the swivel coupling with respect to the other.

The swivel coupling is shown in detail in FIG. 2. One plastic piece 20 has a body 21 which is generally cylindrical and has a hollow interior 22. Projecting coaxially through and beyond the body 21 is a male standard Luer taper 23. The internal surface 24 of the body has a standard Luer thread 25 thereby providing a Luer lock connector. The exterior surface of the body has a plurality of—for example, six—axially extending ribs 26 which permit the body to be securely gripped during the rotation procedure.

In the other end of the body a flange 30 is provided, the flange projecting radially beyond the surface of the body. The flange has a surface 31 tapering toward the end which facilitates the assembly of the piece 20 with respect to the other piece, as will be described below. Projecting beyond the flange 30 is a spigot 33. A shoulder 34 is provided at the junction between the spigot 33 and the flange 30.

The other piece 40 has a body 41 having a socket consisting of a first recess 42 through which the spigot 33 passes, and a second recess 43 into which the spigot passes to stabilize the axial alignment between the pieces 20 and 40 and to prevent cocking of the pieces with respect to each other. A quad O-ring 45 is located in the recess and surrounds the spigot. The O.D. of the O-ring is approximately 0.005 to 0.008 inch greater than the diameter of the recess 42 thereby interfering with the cylindrical surface of the recess. The I.D. is approximately 0.005 inch less than the diameter of the spigot 33 thereby providing radial interference of the O-ring with respect to the spigot. The shoulder 34 is axially spaced from the body 41 a distance equal to or slightly greater than the thickness of the O-ring to permit easy rotation of piece 20 with respect to piece 40.

The body 41 has a collar 47 terminating in an inwardly-directed lip 48 which receives the flange 30 on the first piece 20. The engagement of the flange 30 with the body 41 blocks axial movement of the body 21 with respect to the body 41 thereby avoiding axial compression of the O-ring 45. When in the position illustrated, the lip 48 overhangs the flange 30, thereby capturing the body 21 in the body 41 with a loose fit which permits easy rotation of the elements 20 and 40 with respect to each other.

The body 41 terminates in a male standard Luer taper 50 whereby the piece 40 of the coupling can be connected to the stopcock. Optionally, the device can be provided with a female connection.

In the manufacture of the invention, the two plastic pieces are molded with fairly close tolerances. The O-ring 45 is placed in the recess 42 and the spigot 33 of piece 20 is inserted through the O-ring into the recess 43. The pieces are forced together until the tapered flange rides past the lip 48 of the collar 47. The resilience of the plastic pieces permits a slight flexure to permit the flange to be inserted past the lip 48 whereupon the pieces return to their normal position wherein the flange is captured by the lip. Axial movement of the pieces with respect to each other is blocked by engagement of the flange with the body 41 of the piece 40.

No lubrication of the pieces is required.

The piece 40 is connected to the stopcock system 18 and thus to the source of fluid pressure. The piece 20 is connected to a female standard Luer member on the end of a catheter to connect the coupling to a catheter. The procedure for the radiological catheterization proceeds generally as described above.

During rotation, to insert the catheter into the heart, there is minimal friction between the elements, thus facilitating rotation of piece 20 with respect to piece 40. After the catheter has been inserted, the fluid, radio opaque die is applied by syringe or machine under high pressure. Upon application of the fluid, the O-ring compresses against shoulder 34 thereby expanding against the recess surface and contracting on the spigot. The greater the pressure, the greater the sealing force.

Having described my invention, I claim:

1. A swivel coupling comprising:
   a first plastic body;
   a fluid connection at one end of said body;
   a circular flange projecting radially from the other end of said body;
   a spigot projecting axially from said flange;
   a second plastic body having a socket into which said spigot projects;
   a collar projecting from one end of said body, and surrounding said flange on said first body;
   an inwardly directed lip on said collar capturing said flange to secure said two bodies together;
   said socket having a shoulder;
   a cylindrical recess projecting from said shoulder and surrounding said spigot;
   an O-ring disposed in said recess and being dimensioned to form a seal between said recess and said spigot;
   said shoulder being spaced from said first body by a distance greater than the thickness of said O-ring to permit said bodies to rotate freely with respect to each other; and
   a connector on the opposite end of said second body.

2. A swivel coupling as in claim 1, in which said flange is tapered to facilitate its assembly to said second body.

3. A swivel coupling as in claim 1 or 2, in which said second body has a smaller second recess extending from said shoulder;
   said spigot projecting beyond said O-ring into said second recess to minimize cocking of the bodies with respect to each other.

4. A swivel coupling as in claim 1, in which said O-ring has an outer diameter greater than the diameter of said recess and an inner diameter less than the diameter of said spigot.

5. A swivel coupling as in claim 4, in which the outer diameter of said O-ring is about 0.005–0.008 inch greater than the diameter of said recess and the inner diameter is about 0.005 inch less than the diameter of said spigot.

6. A swivel coupling as in claim 1, in which the connector on said first body is a male standard Luer taper surrounded by a standard Luer thread; and
   the connector on said second body is a male standard Luer taper.

7. In a catheterization system having a catheter to be fed in a tortuous path through a blood vessel, a source of fluid under pressure and a rotatable coupling connecting said fluid source to said catheter;
   the improvement comprising a two-piece plastic swivel coupling in which;
   one piece has a recess and an O-ring disposed within said recess;
   the other piece has a spigot projecting into said recess through said O-ring;
   said O-ring having an interference fit between said spigot and said recess;
   one of said pieces having a collar terminating in a radially inwardly projecting lip of a first diameter, the other of said pieces having a circular flange of slightly greater diameter than said first diameter and underlying said lip when said pieces are forced together axially, whereby said pieces may be snap-fit together by applying axial pressure;
   and means blocking axial movement of one piece with respect to the other to preclude axial compressing of said O-ring;
   whereby said O-ring provides a fluid seal while presenting a minimum of resistance to the rotation of one piece with respect to the other.

8. In a catherization system having a catheter to be fed in a tortuous path through a blood vessel, a source of fluid under pressure and a rotatable coupling connecting said fluid source to said catheter; said rotatable coupling comprising:
   a first plastic body;
   a fluid connection at one end of said body;
   a circular flange projecting radially from the other end of said body;
   a spigot projecting axially from said flange;
   a second plastic body having a socket into which said spigot projects;
   a collar projecting from one end of said body, and surrounding said flange on said first body;
   an inwardly directed lip on said collar capturing said flange to secure said two bodies together;
   said socket having a shoulder;

a cylindrical recess projecting from said shoulder and surrounding said spigot;

an O-ring disposed in said recess and being dimensioned to form a seal between said recess and said spigot;

said shoulder being spaced from said first body by a distance greater than the thickness of said O-ring to permit said bodies to rotate freely with respect to each other; and a connector on the opposite end of said second body.

* * * * *